United States Patent
Holt et al.

(10) Patent No.: US 6,295,252 B1
(45) Date of Patent: Sep. 25, 2001

(54) FIXATING IMAGE IN MIGRATING DYE INDICATOR

(75) Inventors: Robert J. Holt, Cornwall-on-Hudson; David J. Haas, Suffern, both of NY (US)

(73) Assignee: Temtec, Inc., Suffern, NY (US)

( * ) Notice: Subject to any disclaimer, the term of this patent is extended or adjusted under 35 U.S.C. 154(b) by 0 days.

(21) Appl. No.: 09/366,412

(22) Filed: Aug. 4, 1999

(51) Int. Cl.[7] ............................. G04B 17/00; G01N 31/32
(52) U.S. Cl. ........................ 368/327; 116/200; 116/206
(58) Field of Search ............................. 368/10, 121, 327; 116/200, 206, 207, 217, 300

(56) References Cited

U.S. PATENT DOCUMENTS

| | | | |
|---|---|---|---|
| 5,058,088 | * 10/1991 | Haas et al. | 368/327 |
| 5,446,705 | * 8/1995 | Haas et al. | 368/327 |
| 5,633,835 | * 5/1997 | Haas et al. | 368/327 |
| 5,699,326 | * 12/1997 | Haas et al. | 368/327 |
| 5,719,828 | * 2/1998 | Haas et al. | 368/327 |
| 5,930,206 | * 7/1999 | Haas et al. | 368/327 |

* cited by examiner

*Primary Examiner*—Vit Miska
(74) *Attorney, Agent, or Firm*—Michael Zall

(57) ABSTRACT

A migrating dye indicator that includes a display layer and a base substrate layer. An adhesive layer is on one surface of the display layer for adhesively attaching the display layer to the base layer. The base layer includes a migrating dye capable of migrating through the adhesive layer to the display layer when the adhesive layer is placed in contact therewith. The adhesive layer contains an accelerator for enhancing the migration of the dye through the adhesive layer. The base layer contains a means for absorbing the accelerator into the base layer.

9 Claims, 3 Drawing Sheets

FIXATING IMAGE IN MIGRATING DYE INDICATOR

BACKGROUND OF THE INVENTION

1. Field of the Invention

The present invention relates to a migrating dye, ink or colorant indicator, for example, visually changing paper (VCP) or a time indicator, which provides a rapid and clear indicia of expiration, e.g., change in color of the image, and includes a means for fixating the image produced so that it is not blurred.

2. Description of the Related Art

There are numerous type migrating dye indicators. By the use of the term "dye" herein, it is meant an ink, dye or colorant that can be used to print an indicia and is capable of migrating through a specific media. One type of migrating dye indicator is a time indicator which provides, after activation, a visual indication of the passage of an amount of time. Such a time indicator is useful, for example, as a game piece, as a security badge, as an indicator of the length of time a perishable item has been on the wholesaler's or retailer's shelf and for numerous other uses.

U.S. Pat. Nos. 5,058,088 and 4,903,254, both to Haas disclose the use of migrating dyes to develop an image.

U.S. Pat. No. 5,058,088 describes a time indicator which includes a first substrate having first and second surfaces and at least two indicia areas on the first surface. A second substrate having first and second surfaces is also provided. A first chemical agent is provided on each of the indicia areas and a second chemical agent is provided on the first surface of the second substrate. The first surfaces of each substrate overlay and are in contact with each other, the chemical agents coacting to cause a visually perceptible change at one of the second surfaces overlaying the first indicia area in a first selected time interval and a visually perceptible change in said second surface overlaying the second indicia area in a second selected time interval, the first selected time interval differing from the second selected time interval. A preferred embodiment of the time indicator includes an ink pattern of dots printed in a preselected pattern in the indicia area and an adhesive activator means on the first surface of the second substrate. The ink and activator coact to cause the ink pattern of dots to gradually bleed and blend together to cause a visually perceptible change through the second substrate overlaying the indicia area in a selected time interval. Preferred embodiments of the invention are self-timing parking permits and tickets.

U.S. Pat. No. 4,903,254 describes a time indicator for use as a security badge. The badge includes a four-layer front part and a two-layer rear part. The front part has, overlying each other, a transparent front support layer with a front print display surface, an adhesive and ink display layer with a front ink display surface, an optical barrier layer; and an adhesive and ink dissolver layer. The rear part has, overlaying each other, an ink film layer and a backup member layer. Upon issue of the badge, a release sheet is peeled off the ink film layer, and the front part is overlaid and pressed down upon the rear part, with the adhesive and ink dissolver layer and the ink film layer forming an assembly joint therebetween. The time interval then begins and the ink migrates from the ink film layer, in series, through the assembly joint, the ink dissolver layer, the optical barrier layer, the adhesive and ink display layer to the front ink display surface, where it forms expiration notice words and diagonal voiding bars after expiration to the time interval.

Generally, in the aforedescribed technology, a dye is incorporated into a conventional ink and an image printed on a substrate using any conventional printing method. The migration of the dye is activated by applying an overlay (display layer) onto the printed image, the display layer comprising, for example, a pressure sensitive adhesive on a clear plastic sheet. The adhesive may be clear or opaque (usually white). The dye migrates into the adhesive and is seen by the viewer of the display layer. Multiple colors can be developed by using multiple dyes to provide images, symbols or printed messages.

The original printed image maybe hidden by a confusion pattern, an opaque layer, multiple color inks/dyes or any other method known to one skilled in the art. Confusion patterns can be random or pattern dots of migrating and non-migrating inks.

The image development time can be controlled by several factors such as adhesive composition, selection of dye, adhesive thickness, multiple adhesive/polymer layers, and the original printed image. Adhesive additives, i.e., accelerators, such as plasticizers are added to increase the speed of dye migration. Selection of these additives can have an effect on the speed and the final color.

A problem that generally exists with such migrating dye indicators is that the indicia gradually appears and changes color over a period of time and after the indicia appears there is a continuing migration of the dye causing a blurring of the indicia. It thus becomes difficult to ascertain the completion of the time interval and if it is important to read the indicia it becomes blurred and unintelligible. The adhesive contains the accelerator agents that not only increase the speed of image appearance but also increase the speed of image blurring. What is required for such migrating dye indicator is a technology wherein the indicia does not blur after the period of time has elapsed.

Methods have been devised for use in time indicators for preventing the blurring of the image that appears. For example, U.S. Pat. No. 5,446,705 to Haas describes one such method. A time indicator is provided that changes color or produces an image or information after a specific time interval. The time indicator includes a base substrate with colored dye deposited on a first surface; and a substrate having an adhesive on a first surface thereof, the adhesive positioned at discrete locations on the first surface of the substrate. The substrate and the base substrate are put into adhesive contact. The adhesive contacts and coacts the colored dye to dissolve the dye and permit the dye to migrate through the adhesive to cause a color change visible through the substrate. The discrete adhesive inhibits lateral migration of the dye to preserve the image or information of the dye in a clear and/or understandable condition.

This method, in effect, creates a physical barrier that prevents the unwanted migration of the dye. The barrier contains the dye within a specified area. The dye is prevented from horizontal diffusion through the adhesive by the discontinuous pattern of adhesive (dots). Between the dots is an air barrier that prevents the dye from migrating and blurring the image. The dye diffuses within the individual dots adhesive but does not travel any further.

It is desirable under certain circumstances to retain the resulting migrating dye image or indicia for long periods of time without blurring. This is particularly desirable for hidden messages, game pieces, coupons and promotions that benefit from self appearing messages. It is thus highly desirable, and in fact required for some uses that the migrating dye image appear relatively fast and remain legible after long periods of time, e.g., 6 months.

OBJECTS AND SUMMARY OF INVENTION

It is an object of this invention to provide a color change or migrating dye indicator that reveals an image.

It is a further object of this invention to provide an indicator wherein the resulting image will not degrade with time and become blurry.

The objects of this invention are achieved by a migrating dye indicator that includes a display layer and a base substrate layer. An adhesive layer is on one surface of the display layer for adhesively attaching the display layer to the base layer. The base layer includes a migrating dye capable of migrating into the adhesive layer of the display layer when the adhesive layer is placed in contact therewith. The adhesive layer contains an accelerator for enhancing the migration of the dye through the adhesive layer. The base layer contains a means for absorbing the accelerator into the base layer.

Thus, when the adhesive layer on the display layer is contacted with and overlies the base layer, the adhesive layer adhesively attaches the display layer to the base layer. The migrating dye is then activated to migrate into the adhesive layer of the display layer in a period of time to cause the formation of an indicia in the display layer after the period of time has elapsed. Simultaneously, the accelerator is absorbed from the adhesive into the base substrate to inhibit the migration of the dye through the adhesive to thereby minimize the blurring of the indicia after the period of time has elapsed.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF INVENTION

Figure 1:
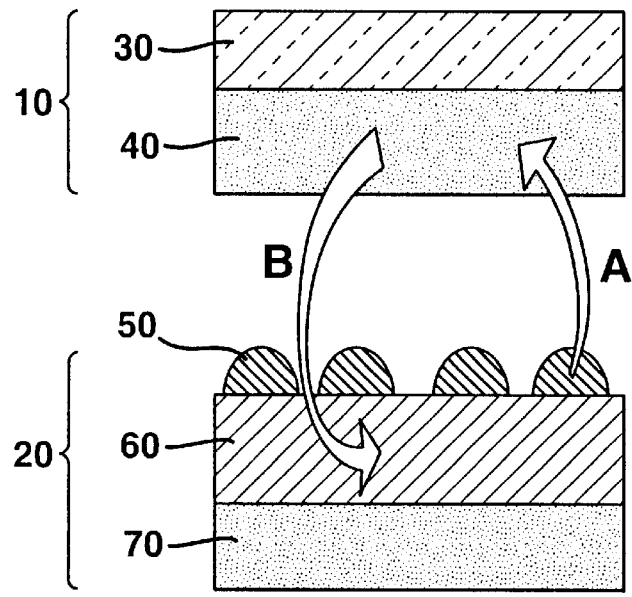
FIG. 1 is a schematic of one embodiment of the migrating dye indicator of this invention.
Figure 3:
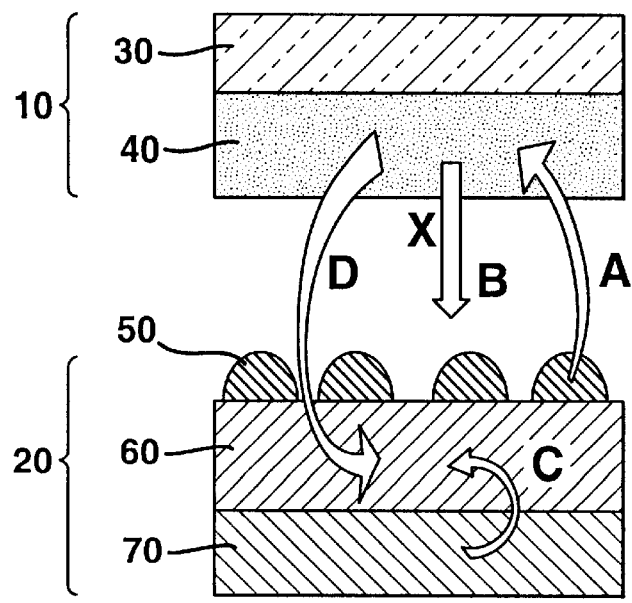
FIG. 3 is a schematic of another embodiment of the migrating dye indicator of this invention.

Referring to FIGS. 1 and 3, the migrating dye indicator comprises a front display part or layer 10 and a base substrate part or layer 20. An adhesive layer 40 is on one surface of the display layer 10 for adhesively attaching the display layer 10 to the base layer 20. The base layer 20 includes a migrating dye or colorant 50 capable of migrating into the adhesive layer 40 to the display layer 10 when the adhesive layer is placed in contact therewith.

The adhesive layer 40 contains an accelerator for enhancing the migration of the dye 50 through the adhesive layer 40. The base layer 20 contains a means for absorbing the accelerator into the base layer 20. Thus, when the adhesive layer 40 on the display layer 10 is contacted with and overlies the base layer 20, the adhesive layer 40 adhesively attaches the display layer 10 to the base layer 20, the migrating dye 50 is activated to migrate through the adhesive layer 40 to the display layer 10 in a period of time to cause the formation of an indicia in the display layer 10 after the period of time has elapsed. Simultaneously, the accelerator is absorbed from the adhesive layer 40 into the base substrate 20 to inhibit the migration of the dye 50 through the adhesive layer 40 to thereby minimize the blurring of the indicia, i.e., "freeze" the image or indicia, after the period of time has elapsed.

Referring to FIGS. 1 and 3, this invention relates to color-changing indicators (10 and 20 combined) that utilize known image producing technology. The improvement consists of the method of "freezing" the image or indicia by removal of the accelerator from the adhesive 40 to inhibit or prevent further migration of the dye 50 after the image forms.

Typically, the accelerator used in the adhesive 40 is used to assist the migration of the dyes 50 through the adhesive 40. The accelerators are typically organic liquids, such as plasticizers, that allow and accelerate the migration of dye into and through the adhesive 40. Without such accelerator agents in the adhesive 40, the dye 50 does not migrate through the adhesive 40 to form an indicia or image or migrates at a very slow, unacceptable rate.

In this invention, the adhesive (without the accelerator) is chosen such that the migration of the colorant or dye is either nonexistent or extremely slow. Accelerator agents are then selected, inter alia, to improve the migration rate of the colorant or dye so that an image can be formed in the display lay 10 in the selected period of time.

Figure 2:
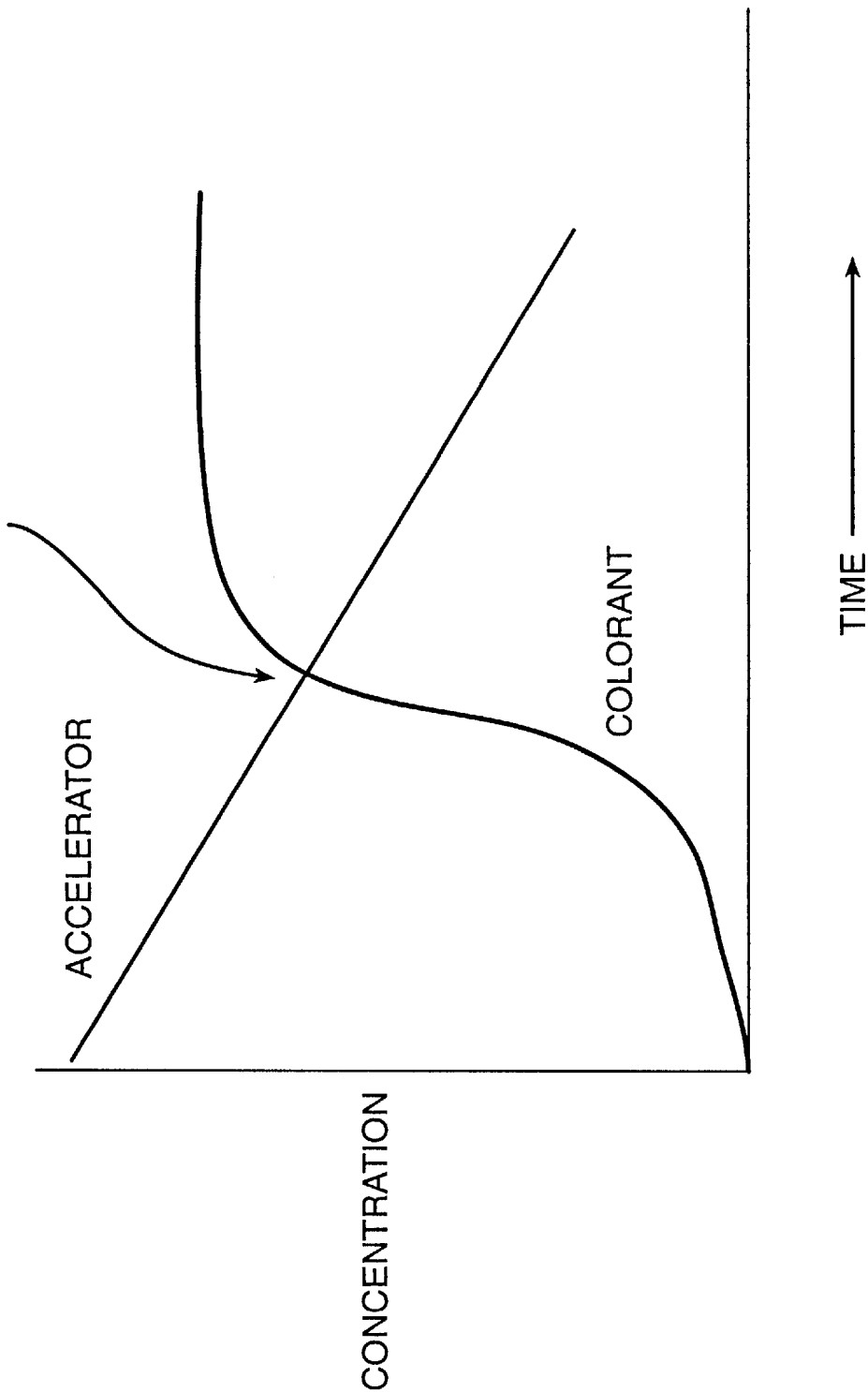
FIG. 2 is a schematic graph of the concentration of accelerator in the adhesive and colorant or dye in the adhesive versus time after activation for the embodiment depicted in FIG. 1.
Figure 4:
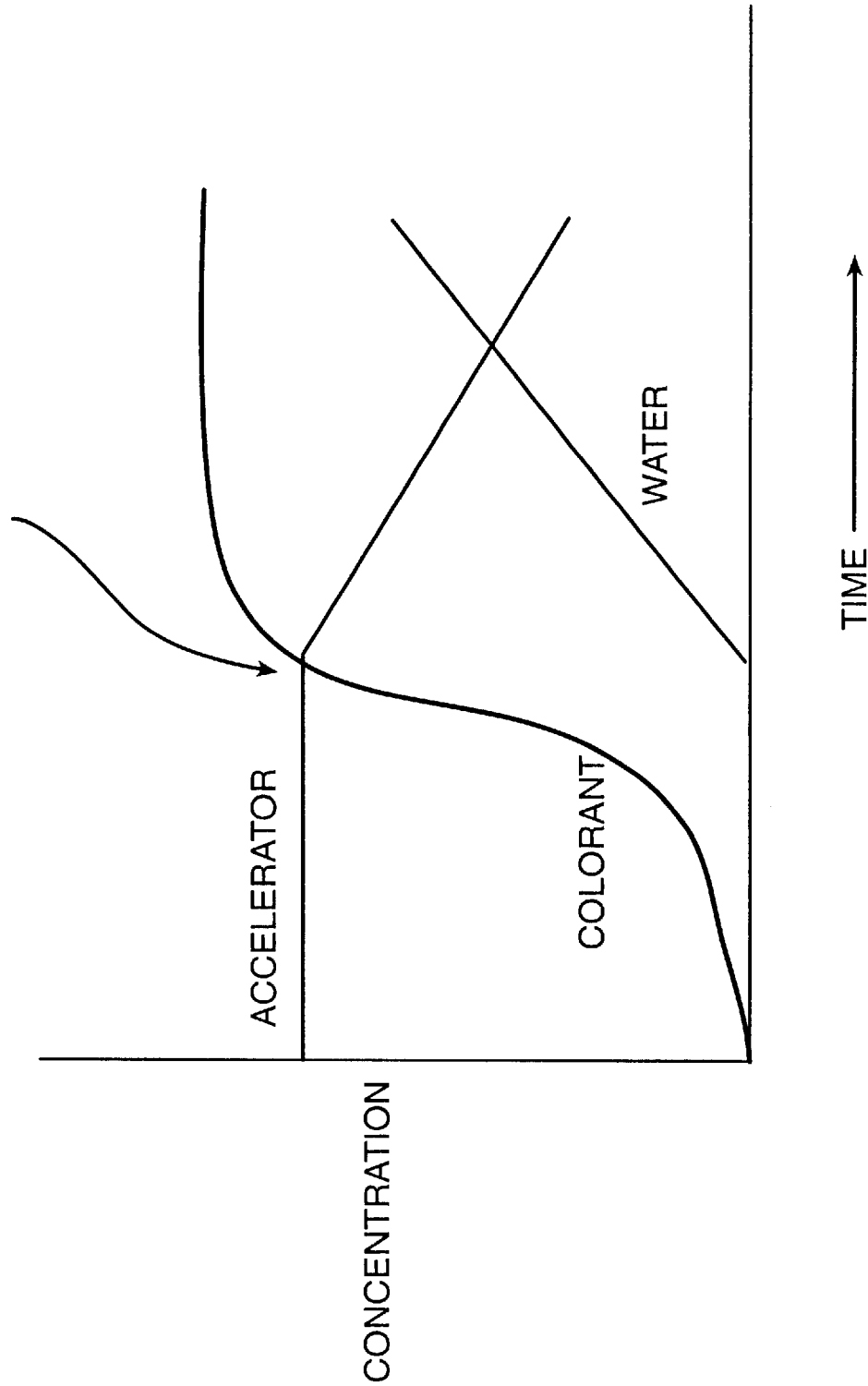
FIG. 4 is a schematic graph of the concentration of accelerator in the adhesive, colorant or dye in the adhesive, and water in the base substrate versus time after activation for the embodiment depicted in FIG. 3.

The base substrate layer 20 that the colorant or dye 50 is printed on is selected in the embodiment depicted in FIGS. 1 and 2, to absorb the accelerator agent in a timely manner from the adhesive layer 40 or, as depicted in FIGS. 3 and 4, be able to change its absorption properties by the addition of a component.

The absorption of the accelerator from the adhesive layer 40 slows the dye migration to freeze the image. The dye migration times are generally shorter than the time required to absorb a sufficient amount of accelerator agent from the adhesive layer 40 to freeze the image. After a sufficient amount of accelerator agent is removed from the adhesive layer 40, the migration rate of the dye through the layer slows or stops, essentially freezing the image in the adhesive layer 40.

EXAMPLES

In the specific examples that follow, dyes were incorporated into flexographic inks and a dot pattern printed on a plain paper label base layer 20. A clear pressure sensitive adhesive layer 40 on a clear polyester sheet 30 was placed over the dot pattern and the dye was allowed to migrate through the adhesive layer 40.

Example 1

A water emulsion adhesive composed of a vinyl acrylic pressure sensitive adhesive, Covinax 081-01 (Franklin International, Columbus, Ohio) and a compatible plasticizer (accelerator) (Polyethylene Glycol 400, Carbowax 400, Union Carbide, Danbury, Conn.) was prepared and applied to the polyester sheet 30. The plasticizer (accelerator) comprised about 20% polyethylene glycol 400 and 80% Covinax 081-01 (wet weight %).

The plain paper label base layer 20 was printed with an ink containing the dye (FD&C Red #3, Pylam, Tempe, Ariz. The clear display layer 10 formed from the polyester sheet 30 with the adhesive layer thereon, including the accelerator, was placed over the printed plain paper label base layer 20 and allowed to stand. After the image was produced, the dye began to diffuse laterally for a small distance and stopped.

A clear visual image was produced and remained constant over a period of time. Visual evidence indicated that the accelerator was absorbed into the base layer. In other examples, various degrees of blurring/migration were seen depending on the dye and its interaction with the adhesive.

Example 2

A water emulsion adhesive composed of a vinyl acrylic pressure sensitive adhesive, Covinax 081-01 (Franklin International, Columbus, Ohio) and a compatible plasticizer (accelerator) of 20% dibutyl phthalate plasticizer, Plasthall DBP (C.P. Hall, Chicago, Ill.) was prepared and applied to the polyester sheet 30.

The plain paper label base layer 20 was printed with an ink containing the dye (FD&C Red #3, Pylam, Tempe, Ariz. The clear display layer 10 formed from the polyester sheet 30 with the adhesive layer thereon, including the accelerator, was placed over the printed plain paper label base layer 20 and allowed to stand. After the image was produced, the dye began to diffuse laterally for a small distance. A clear visual image was produced and eventually blurred over a period of time. Visual evidence indicated that substantially no accelerator was absorbed into the base layer.

Example 3

An adhesive composed of Polytac 213 (H&N Chemical Company, Totowa, N.J.) and a compatible plasticizer (accelerator) of 20% glutarate plasticizer, Plasthall 7050 (C.P. Hall, Chicago, Ill.) was prepared and applied to the polyester sheet 30.

The plain paper label base layer 20 was printed with an ink containing the dye (FD&C Red #3, Pylam, Tempe, Ariz.). The clear display layer 10 formed from the polyester sheet 30 with the adhesive layer thereon, including the accelerator, was placed over the printed plain paper label base layer 20 and allowed to stand. After the image was produced, the dye began to diffuse laterally for a small distance. A clear visual image was produced and eventually blurred over a period of time. Visual evidence indicated that substantially no accelerator was absorbed into the base layer.

A polar dye such FD&C Red #3 will migrate in a polar plasticized acrylic pressure sensitive adhesive (PEG 400—see Example 1 above). If the adhesive changes to a less polar environment, by removal of PEG 400, the polar dye would stop migrating.

Another example of a polar dye is Alizarine Fast Blue CL (C.I. Acid Blue 25) from Compton & Knowles.

Other examples of appropriate pressure sensitive adhesives, i.e., adhesives that do not allow the dye to migrate without an appropriate accelerator, are rubber-based adhesives.

The migration rate of the dye is largely dependent on the migrating environment in the adhesive layer. If the dye is not compatible with the environment in the adhesive layer, it will not migrate. Any change in the environment will change the migration rate, by either increasing or decreasing the rate.

It has thus been found that the dye will migrate until it encounters a new environment or region in the adhesive layer. If this new region or environment is incompatible with the dye it does not allow the dye to migrate. This in order to "freeze" or fixate the image a discrete dots of adhesive, a "chemical incompatibility wall" is created. This is achieved by removing the accelerator agent from the adhesive environment. The removal of the accelerator from the adhesive changes the adhesive environment sufficiently to inhibit or prevent continued dye migration to fixate the image. Thus, when the polar accelerator is removed it decreases the polarity of the adhesive environment to prevent or inhibit the further migration of a polar dye and thus fixate the image.

In the above described embodiment, the environment changed because the base paper substrate 60 absorbed the accelerator agent, e.g., plasticizer—polyethylene glycol.

Referring to FIGS. 3 and 4, in yet another embodiment, a second agent 70, e.g., water, can be introduced into the base substrate 60 to increases the ability of the substrate to absorb the accelerator agent. In the case of the introduction of water, the accelerator, being very polar would easily and quickly diffuse into the water phase formed in the base substrate 60. Prior to water introduction, the accelerator would have little or no absorption into the substrate.

Such an application would be useful for a "diaper-dry" time indicator. Upon putting on the diaper, the indicator is activated. Several images will develop over time at certain intervals. The child wets the diaper and the fluid is channeled to the base substrate 60 of the indicator. The base substrate 60 becomes wet, changing the polar absorption properties of the base substrate 60. The polar accelerator agent is then absorbed into the base substrate 60 and the dye migration rate slows or stops. The number of developing images would show the passage of time. Another indication can be the distance the dye travels would indicate the passage of time the diaper was on until the child wets. This indicator can be used as an aid in toilet training.

Modifications of the foregoing may be made without departing from the spirit and scope of the invention. What is desired to be protected by Letters Patents is set forth in the appended claims.

What is claimed is:

1. A migrating dye indicator comprising:
    a display layer;
    a base substrate layer;
    an adhesive layer on one surface of the display layer for adhesively attaching the display layer to the base layer;
    the base layer including a migrating dye capable of migrating into the adhesive layer of the display layer when the adhesive layer is placed in contact therewith;
    the adhesive layer containing an accelerator for enhancing the migration of the dye through the adhesive layer;
    the base layer containing a means for absorbing the accelerator into the base layer;
    whereby when the adhesive layer on the display layer is contacted with and overlies the base layer, the adhesive layer adhesively attaches the display layer to the base layer, the migrating dye is activated to migrate into the adhesive layer of the display layer in a period of time to cause the formation of an indicia in the display layer after the period of time has elapsed, and the accelerator is absorbed from the adhesive layer into the base substrate to inhibit the migration of the dye through the adhesive layer to thereby minimize the blurring of the indicia after the period of time has elapsed.

2. The migrating dye indicator of claim 1, wherein the adhesive layer is a water emulsion adhesive.

3. The migrating dye indicator of claim 2, wherein the water emulsion adhesive is a vinyl acrylic pressure sensitive adhesive.

4. The migrating dye indicator of claim 2, wherein the adhesive is an acrylic based adhesive.

5. The migrating dye indicator of claim 2, wherein the adhesive is a rubber based adhesive.

6. The migrating dye indicator of claim 1, wherein the accelerator comprises polyethylene glycol.

7. A migrating dye indicator comprising:

a display layer;

a base substrate layer;

an adhesive layer on one surface of the display layer for adhesively attaching the display layer to the base layer;

the base layer including a migrating polar dye capable of migrating through the adhesive layer to the display layer when the adhesive layer is placed in contact therewith;

the adhesive layer containing a polar accelerator for enhancing the migration of the dye through the adhesive layer;

the base layer containing a means for absorbing the accelerator into the base layer;

whereby when the adhesive layer on the display layer is contacted with and overlies the base layer, the adhesive layer adhesively attaches the display layer to the base layer, the migrating dye is activated to migrate through the adhesive layer to the display layer in a period of time to cause the formation of an indicia in the display layer after the period of time has elapsed, and the accelerator is absorbed from the adhesive layer into the base substrate to inhibit the migration of the dye through the adhesive layer to thereby minimize the blurring of the indicia after the period of time has elapsed.

8. A migrating dye indicator comprising:

a display layer;

a base substrate layer;

an adhesive layer on one surface of the display layer for adhesively attaching the display layer to the base layer;

the base layer including a migrating polar dye capable of migrating through the adhesive layer to the display layer when the adhesive layer is placed in contact therewith;

the adhesive layer containing a polar accelerator for enhancing the migration of the dye through the adhesive layer;

the base layer containing an aqueous composition for enhancing the absorption of the accelerator into the base layer;

whereby when the adhesive layer on the display layer is contacted with and overlies the base layer, the adhesive layer adhesively attaches the display layer to the base layer, the migrating dye is activated to migrate through the adhesive layer to the display layer in a period of time to cause the formation of an indicia in the display layer after the period of time has elapsed, and the accelerator is absorbed from the adhesive layer into the base substrate to inhibit the migration of the dye through the adhesive layer to thereby minimize the blurring of the indicia after the period of time has elapsed.

9. A diaper having a migrating dye indicator comprising:

a diaper;

a base substrate layer mounted to the diaper;

a display layer;

an adhesive layer on one surface of the display layer for adhesively attaching the display layer to the base layer;

the base layer including a migrating polar dye capable of migrating through the adhesive layer to the display layer when the adhesive layer is placed in contact therewith;

the adhesive layer containing a polar accelerator for enhancing the migration of the dye through the adhesive layer;

the base layer capable of absorbing aqueous body fluids therein, to thereby enhance the absorption of the accelerator into the base layer;

whereby when the adhesive layer on the display layer is contacted with and overlies the base layer, the adhesive layer adhesively attaches the display layer to the base layer, the migrating dye is activated to migrate through the adhesive layer to the display layer to cause the continued formation of an indicia in the display layer, and when the base layer absorbs the aqueous body fluids the accelerator is absorbed from the adhesive layer into the base substrate to inhibit the further migration of the dye through the adhesive layer to thereby fixate the indicia to indicate that the diaper has been wetted with bodily fluids.

* * * * *